US007695434B2

(12) United States Patent  
Malecha (10) Patent No.: US 7,695,434 B2  
(45) Date of Patent: Apr. 13, 2010

(54) MEDICAL DEVICE FOR PREDICTING A USER'S FUTURE GLYCEMIC STATE

(75) Inventor: Michael Malecha, Muir of Ord (GB)

(73) Assignee: Lifescan Scotland, Ltd. (GB)

( * ) Notice: Subject to any disclaimer, the term of this patent is extended or adjusted under 35 U.S.C. 154(b) by 0 days.

(21) Appl. No.: 11/875,563

(22) Filed: Oct. 19, 2007

(65) Prior Publication Data

US 2009/0105573 A1 Apr. 23, 2009

(51) Int. Cl.
*A61B 5/00* (2006.01)
*A61B 5/05* (2006.01)
(52) U.S. Cl. .................................... 600/365; 600/347
(58) Field of Classification Search .............. 600/316, 600/319, 347, 365
See application file for complete search history.

(56) References Cited

U.S. PATENT DOCUMENTS

| 5,482,035 | A | | 1/1996 | Paloheimo |
| 5,792,062 | A | * | 8/1998 | Poon et al. ................ 600/509 |
| 5,840,020 | A | | 11/1998 | Heinonen et al. |
| 6,041,398 | A | | 3/2000 | Pechanek et al. |
| 6,272,480 | B1 | | 8/2001 | Tresp et al. |
| 6,379,301 | B1 | | 4/2002 | Worthington et al. |
| 6,421,633 | B1 | | 7/2002 | Heinonen et al. |
| 6,653,091 | B1 | | 11/2003 | Dunn et al. |
| 6,882,940 | B2 | | 4/2005 | Potts et al. |
| 6,923,763 | B1 | | 8/2005 | Kovatchev et al. |

(Continued)

FOREIGN PATENT DOCUMENTS

EP 1102194 A2 5/2001

OTHER PUBLICATIONS

Thomas Briegel, et al., "A Nonlinear State Space Model for the Blood Glucose Metabolism of a Diabetic", Anwendungsaufsatz, pp. 228-236, Automatisierungstechnik 50, May 2002, Oldenbourg Verlag.

(Continued)

*Primary Examiner*—Charles A Marmor, II
*Assistant Examiner*—Christian Y Jang (57) ABSTRACT

A medical device for predicting a user's future glycemic state includes a memory module, a processor module and a user alert module. The memory module is configured to receive and store a plurality of glucose concentrations as a function of time that were generated by a user's use of a continuous glucose monitor. The processor module is configured to derive first and second glucose prediction equations that are fits to the plurality of glucose concentrations stored in the memory module with the fits being based on first and second mathematical models, respectively. The processor module is also configured to calculate first and second predicted glucose concentrations at a future time using the first and second glucose prediction equations, respectively, and to also calculate an average predicted glucose concentration and a merit index based on the first and second predicted glucose calculations. The processor module is further configured to input the plurality of glucose concentrations as a function of time, the average predicted glucose concentration and the merit index into a trained model (e.g., a Hidden Markov Model) that outputs a set of glucose concentration probabilities for the future time and to then predict the user's future glycemic state based on the set of glucose concentration probabilities. The user alert module is configured to alert the user in a manner dependent on the predicted user's future glycemic state.

7 Claims, 5 Drawing Sheets

U.S. PATENT DOCUMENTS

| | | | |
|---|---|---|---|
| 7,011,630 | B2 | 3/2006 | Desai et al. |
| 7,025,425 | B2 | 4/2006 | Kovatchev et al. |
| 7,167,818 | B2 | 1/2007 | Brown |
| 2003/0028089 | A1 | 2/2003 | Galley et al. |
| 2003/0050546 | A1* | 3/2003 | Desai et al. ............ 600/347 |
| 2004/0133081 | A1* | 7/2004 | Teller et al. ............ 600/300 |
| 2004/0248204 | A1 | 12/2004 | Moerman |
| 2005/0197621 | A1 | 9/2005 | Poulsen et al. |
| 2005/0214892 | A1 | 9/2005 | Kovatchev et al. |
| 2005/0240356 | A1 | 10/2005 | Staib et al. |

OTHER PUBLICATIONS

Sean R. Eddy, "What is a Hidden Markov Model?", Nature Biotechnology, pp. 1315-1316, vol. 22, No. 10, Oct. 2004.

Alex Pentland, "Healthwear: Medical Technology Becomes Wearable", Computer, pp. 42-49, vol. 37, No. 5, May 2004.

Sam Roweis, "SCIA 2003 Tutorial: Hidden Markov Models", University of Toronto, 10 pages, Jun. 29, 2003.

Volker Tresp, et al., "Neural-Network Models for the Blood Glucose Metabolism of a Diabetic", IEEE Transactions on Neural Networks, pp. 1204-1213, vol. 10, No. 5, Sep. 1999.

* cited by examiner

| FIG. 2A | FIG. 2B |

|  | Hypoglycemia | | Normoglycemia | | |
| --- | --- | --- | --- | --- | --- |
| mg/dL | 1-50 | 51-70 | 71-120 | 121-170 | 171-179 |
| 1 | 0.0011 | 0.0095 | 0.0370 | 0.0000 | 0.0000 |
| 2 | 0.0011 | 0.0190 | 0.0540 | 0.0000 | 0.0000 |
| 3 | 0.0000 | 0.0169 | 0.0487 | 0.0000 | 0.0000 |
| 4 | 0.0021 | 0.0190 | 0.0455 | 0.0000 | 0.0000 |
| 5 | 0.0021 | 0.0222 | 0.0476 | 0.0000 | 0.0000 |
| 6 | 0.0011 | 0.0169 | 0.0000 | 0.0000 | 0.0000 |
| 7 | 0.0011 | 0.0190 | 0.0000 | 0.0000 | 0.0000 |
| 8 | 0.0011 | 0.0190 | 0.0000 | 0.0000 | 0.0000 |
| 9 | 0.0032 | 0.0148 | 0.0000 | 0.0000 | 0.0000 |
| 10 | 0.0032 | 0.0212 | 0.0000 | 0.0000 | |
| 11 | 0.0021 | 0.0233 | 0.0000 | 0.0000 | |
| 12 | 0.0053 | 0.0254 | 0.0000 | 0.0000 | |
| 13 | 0.0042 | 0.0243 | 0.0000 | 0.0000 | |
| 14 | 0.0042 | 0.0402 | 0.0000 | 0.0000 | |
| 15 | 0.0021 | 0.0275 | 0.0000 | 0.0000 | |
| 16 | 0.0053 | 0.0317 | 0.0000 | 0.0000 | |
| 17 | 0.0032 | 0.0381 | 0.0000 | 0.0000 | |
| 18 | 0.0063 | 0.0317 | 0.0000 | 0.0000 | |
| 19 | 0.0042 | 0.0328 | 0.0000 | 0.0000 | |
| 20 | 0.0032 | 0.0476 | 0.0000 | 0.0000 | |
| 21 | 0.0042 | | 0.0000 | 0.0000 | |
| 22 | 0.0074 | | 0.0000 | 0.0000 | |
| 23 | 0.0000 | | 0.0000 | 0.0000 | |
| 24 | 0.0032 | | 0.0000 | 0.0000 | |
| 25 | 0.0042 | | 0.0000 | 0.0000 | |
| 26 | 0.0000 | | 0.0000 | 0.0000 | |
| 27 | 0.0011 | | 0.0000 | 0.0000 | |
| 28 | 0.0042 | | 0.0000 | 0.0000 | |
| 29 | 0.0021 | | 0.0000 | 0.0000 | |
| 30 | 0.0053 | | 0.0000 | 0.0000 | |
| 31 | 0.0074 | | 0.0000 | 0.0000 | |
| 32 | 0.0169 | | 0.0000 | 0.0000 | |
| 33 | 0.0085 | | 0.0000 | 0.0000 | |
| 34 | 0.0116 | | 0.0000 | 0.0000 | |
| 35 | 0.0085 | | 0.0000 | 0.0000 | |
| 36 | 0.0085 | | 0.0000 | 0.0000 | |
| 37 | 0.0074 | | 0.0000 | 0.0000 | |
| 38 | 0.0042 | | 0.0000 | 0.0000 | |
| 39 | 0.0032 | | 0.0000 | 0.0000 | |
| 40 | 0.0053 | | 0.0000 | 0.0000 | |
| 41 | 0.0032 | | 0.0000 | 0.0000 | |
| 42 | 0.0053 | | 0.0000 | 0.0000 | |
| 43 | 0.0053 | | 0.0000 | 0.0000 | |
| 44 | 0.0095 | | 0.0000 | 0.0000 | |
| 45 | 0.0085 | | 0.0000 | 0.0000 | |
| 46 | 0.0095 | | 0.0000 | 0.0000 | |
| 47 | 0.0116 | | 0.0000 | 0.0000 | |
| 48 | 0.0159 | | 0.0000 | 0.0000 | |
| 49 | 0.0138 | | 0.0000 | 0.0000 | |
| 50 | 0.0148 | | 0.0000 | 0.0000 | |

FIG. 2A

| Hyperglycemia | | | | | | | |
|---|---|---|---|---|---|---|---|
| 180-230 | 231-280 | 281-330 | 331-380 | 381-455 | 456-505 | 506-580 | 581-600 |
| 0.0163 | 0.0096 | 0.0029 | 0.0023 | 0.0000 | 0.0000 | 0.0000 | 0.0003 |
| 0.0123 | 0.0050 | 0.0026 | 0.0006 | 0.0003 | 0.0003 | 0.0000 | 0.0000 |
| 0.0128 | 0.0061 | 0.0026 | 0.0012 | 0.0006 | 0.0000 | 0.0000 | 0.0009 |
| 0.0117 | 0.0067 | 0.0035 | 0.0018 | 0.0003 | 0.0000 | 0.0000 | 0.0000 |
| 0.0128 | 0.0061 | 0.0032 | 0.0003 | 0.0003 | 0.0000 | 0.0000 | 0.0006 |
| 0.0128 | 0.0053 | 0.0044 | 0.0003 | 0.0009 | 0.0000 | 0.0000 | 0.0000 |
| 0.0137 | 0.0070 | 0.0026 | 0.0009 | 0.0003 | 0.0000 | 0.0000 | 0.0006 |
| 0.0143 | 0.0061 | 0.0020 | 0.0020 | 0.0003 | 0.0000 | 0.0000 | 0.0000 |
| 0.0158 | 0.0053 | 0.0023 | 0.0020 | 0.0000 | 0.0000 | 0.0000 | 0.0000 |
| 0.0158 | 0.0058 | 0.0055 | 0.0009 | 0.0006 | 0.0000 | 0.0000 | 0.0000 |
| 0.0117 | 0.0061 | 0.0032 | 0.0012 | 0.0000 | 0.0000 | 0.0000 | 0.0000 |
| 0.0149 | 0.0064 | 0.0058 | 0.0009 | 0.0000 | 0.0000 | 0.0000 | 0.0003 |
| 0.0128 | 0.0079 | 0.0053 | 0.0006 | 0.0000 | 0.0000 | 0.0000 | 0.0000 |
| 0.0143 | 0.0073 | 0.0035 | 0.0015 | 0.0000 | 0.0000 | 0.0000 | 0.0000 |
| 0.0108 | 0.0076 | 0.0032 | 0.0020 | 0.0009 | 0.0000 | 0.0003 | 0.0000 |
| 0.0137 | 0.0061 | 0.0032 | 0.0006 | 0.0006 | 0.0000 | 0.0000 | 0.0009 |
| 0.0155 | 0.0047 | 0.0026 | 0.0015 | 0.0003 | 0.0000 | 0.0000 | 0.0006 |
| 0.0114 | 0.0035 | 0.0044 | 0.0006 | 0.0009 | 0.0000 | 0.0000 | 0.0000 |
| 0.0120 | 0.0047 | 0.0015 | 0.0009 | 0.0003 | 0.0000 | 0.0003 | 0.0003 |
| 0.0163 | 0.0061 | 0.0029 | 0.0003 | 0.0003 | 0.0000 | 0.0000 | 0.0000 |
| 0.0096 | 0.0041 | 0.0035 | 0.0015 | 0.0000 | 0.0000 | 0.0000 | 0.0003 |
| 0.0076 | 0.0023 | 0.0023 | 0.0000 | 0.0000 | 0.0000 | 0.0000 | |
| 0.0111 | 0.0050 | 0.0029 | 0.0009 | 0.0000 | 0.0000 | 0.0000 | |
| 0.0125 | 0.0064 | 0.0026 | 0.0006 | 0.0000 | 0.0000 | 0.0000 | |
| 0.0123 | 0.0041 | 0.0032 | 0.0006 | 0.0000 | 0.0000 | 0.0000 | |
| 0.0093 | 0.0044 | 0.0035 | 0.0006 | 0.0000 | 0.0000 | 0.0000 | |
| 0.0082 | 0.0041 | 0.0018 | 0.0009 | 0.0000 | 0.0000 | 0.0000 | |
| 0.0128 | 0.0053 | 0.0015 | 0.0000 | 0.0003 | 0.0000 | 0.0000 | |
| 0.0090 | 0.0070 | 0.0020 | 0.0009 | 0.0003 | 0.0000 | 0.0000 | |
| 0.0082 | 0.0067 | 0.0026 | 0.0003 | 0.0000 | 0.0000 | 0.0000 | |
| 0.0082 | 0.0073 | 0.0023 | 0.0003 | 0.0003 | 0.0000 | 0.0000 | |
| 0.0114 | 0.0047 | 0.0023 | 0.0012 | 0.0000 | 0.0000 | 0.0000 | |
| 0.0108 | 0.0076 | 0.0020 | 0.0009 | 0.0000 | 0.0000 | 0.0000 | |
| 0.0125 | 0.0058 | 0.0015 | 0.0009 | 0.0000 | 0.0000 | 0.0000 | |
| 0.0096 | 0.0053 | 0.0015 | 0.0009 | 0.0000 | 0.0000 | 0.0000 | |
| 0.0093 | 0.0053 | 0.0012 | 0.0012 | 0.0000 | 0.0003 | 0.0003 | |
| 0.0082 | 0.0032 | 0.0018 | 0.0003 | 0.0000 | 0.0000 | 0.0000 | |
| 0.0096 | 0.0035 | 0.0015 | 0.0006 | 0.0000 | 0.0000 | 0.0003 | |
| 0.0123 | 0.0038 | 0.0029 | 0.0006 | 0.0000 | 0.0000 | 0.0000 | |
| 0.0079 | 0.0023 | 0.0018 | 0.0009 | 0.0000 | 0.0003 | 0.0000 | |
| 0.0070 | 0.0038 | 0.0020 | 0.0006 | 0.0000 | 0.0000 | 0.0000 | |
| 0.0102 | 0.0047 | 0.0012 | 0.0006 | 0.0000 | 0.0000 | 0.0000 | |
| 0.0076 | 0.0035 | 0.0018 | 0.0006 | 0.0003 | 0.0000 | 0.0000 | |
| 0.0070 | 0.0044 | 0.0015 | 0.0003 | 0.0006 | 0.0000 | 0.0000 | |
| 0.0073 | 0.0023 | 0.0018 | 0.0012 | 0.0000 | 0.0000 | 0.0000 | |
| 0.0079 | 0.0029 | 0.0020 | 0.0012 | 0.0000 | 0.0000 | 0.0000 | |
| 0.0076 | 0.0032 | 0.0015 | 0.0000 | 0.0000 | 0.0000 | 0.0000 | |
| 0.0093 | 0.0026 | 0.0006 | 0.0009 | 0.0000 | 0.0000 | 0.0003 | |
| 0.0064 | 0.0038 | 0.0009 | 0.0006 | 0.0000 | 0.0000 | 0.0000 | |
| 0.0085 | 0.0041 | 0.0018 | 0.0000 | 0.0000 | 0.0000 | 0.0003 | |

MEDICAL DEVICE FOR PREDICTING A USER'S FUTURE GLYCEMIC STATE

BACKGROUND OF THE INVENTION

1. Field of the Invention

The present invention relates, in general, to medical devices and, in particular, to glycemic state prediction devices, kits and associated methods.

2. Description of Related Art

Patients with diabetes can find it difficult to maintain their glucose concentration in a preferred euglycemic state (i.e., a glucose concentration the range of between about 70 mg/dL and 180 mg/dL, also referred to as normoglycemic). As a consequence, such patients may experience deleterious hypoglycemic and hyperglycemic states. Reducing the number of wide swings in glucose concentration is believed to significantly reduce the occurrence of long term diabetes-related complications such as blindness, kidney failure, retinopathy, and heart disease.

Continuous glucose monitors (CGM's) have been developed to frequently and conveniently measure a patient's glucose concentration by automatically collecting a large number of glucose concentrations over an extended time duration. Therefore, a patient using a CGM has the opportunity to dose themselves with relatively frequent insulin injections and, thereby, effectively regulate their glucose concentration.

However, a potential drawback of more frequent insulin injections is an increase in the likelihood of the patient inadvertently entering a hypoglycemic state. Hypoglycemic states are dangerous because they can result in a loss of consciousness and, in some instances, death.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements, of which:

DETAILED DESCRIPTION OF ILLUSTRATIVE EMBODIMENTS

The following detailed description should be read with reference to the drawings, in which like elements in different drawings are identically numbered. The drawings, which are not necessarily to scale, depict selected exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Figure 1:
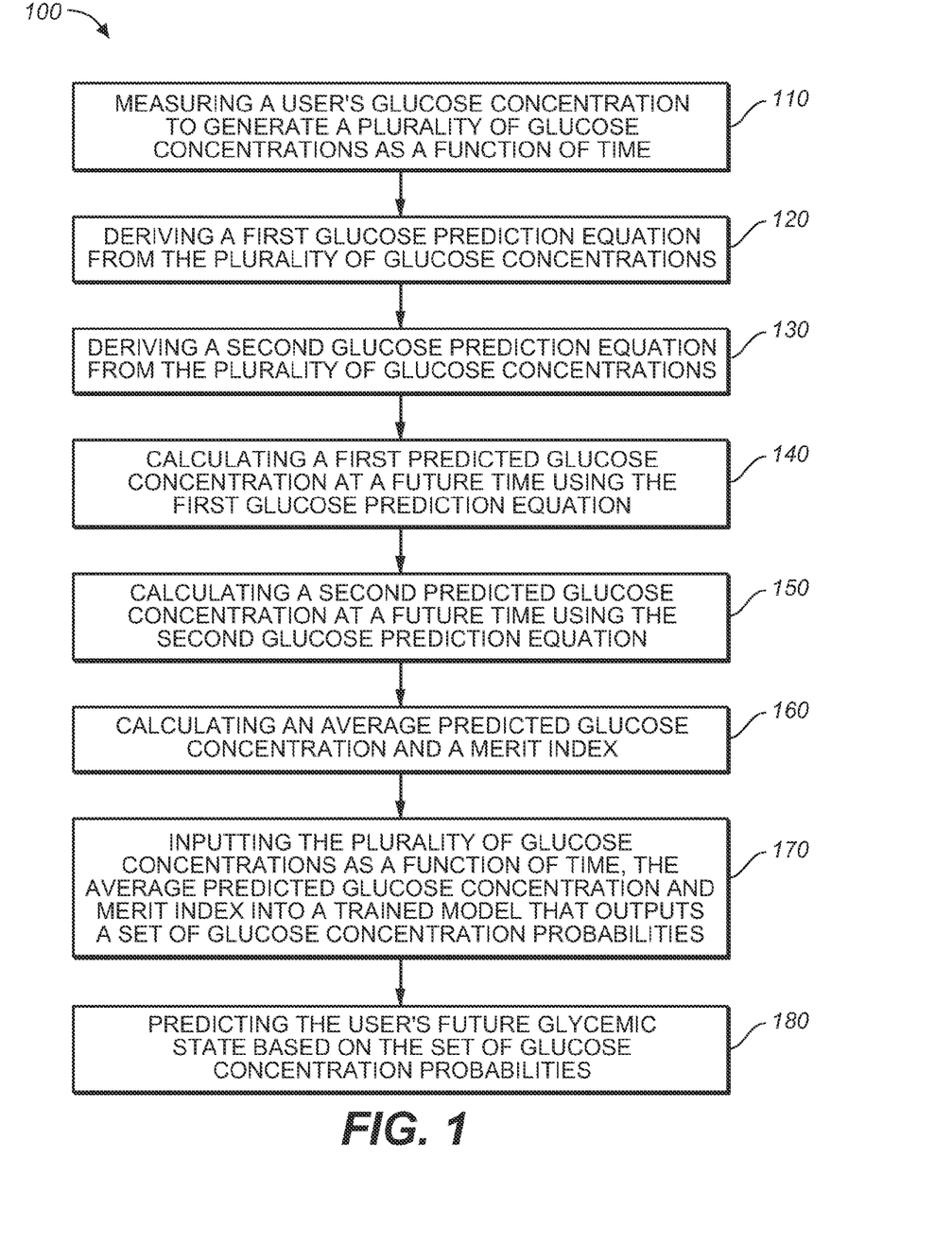
FIG. 1 is a flow diagram depicting stages in process according to an exemplary embodiment of the present invention.

FIG. 1 is a flow diagram depicting stages in method 100 for predicting a user's future glycemic state according to an exemplary embodiment of the present invention. In this regard, one skilled in the art will recognize that a user's future glycemic state can be generally categorized as being one of three possible states, i.e., hypoglycemia, euglycemia, or hyperglycemia. Methods according to embodiments of the present invention (including method 100) employ measurements and algorithms (for example, mathematical equations, mathematical models and statistical models) to assess the probability of a user entering one of these three states, or other glucose concentration ranges, at a future time.

At step 110 of method 100, a user's glucose concentration (e.g., blood glucose concentration) is measured at intervals over a predetermined time duration, thereby generating a plurality of glucose concentrations as a function of time (i.e., a series of glucose concentrations, with each glucose concentration in the series being associated with a time at which that particular glucose concentration was measured).

The predetermined time duration can be, for example, in the range of about 10 minutes to about 30 minutes. The intervals can be either predetermined or determined dynamically based on previous measurements. Typical, but non-limiting, predetermined intervals are in the range of 0.2 minutes to 1 minute (in other words a single measurement is made every 0.2 minutes to every 1 minute during the predetermined time duration).

Step 110 can be accomplished, for example, using any suitable continuous glucose monitor (CGM) known to one skilled in the art. A non-limiting example of a CGM that can be employed in embodiments of the present invention is the Guardian® RT Continuous Monitoring System (commercially available from Medtronic MiniMed, Northridge, Calif. 91325-1219).

If desired, the plurality of glucose concentrations as a function of time can be converted into a unitless plurality if glucose concentrations as a function of time by employing the following equation:

$$g(t_i) = \frac{G(t_i) - G(t_{min})}{G(t_{max}) - G(t_{min})} \qquad \text{Eq. 1}$$

where:

$t_i$=a value of time during the pre-determined time duration;

$t_{min}$=the time when the glucose concentration was the smallest in magnitude during the pre-determined time duration;

$t_{max}$=the time when the glucose concentration was the largest in magnitude during the pre-determined time duration;

$G(t_i)$=glucose concentration at time $t_i$;

$G(t_{min})$=smallest magnitude glucose concentration;

$G(t_{max})$=largest magnitude glucose concentration;

$g(t_i)$=unit glucose concentration at time $t_i$; and i=time interval variable incrementing between the start and the end of the predetermined time duration Moreover, time $t_i$ may be time shifted with respect to the initial time $t_{int}$ of the pre-determined time interval as follows:

$$t_{i\,shift} = t_i - t_{int} \qquad \text{Eq. 2}$$

where:

$t_{ishift}$ = a shifted time value; and $t_{int}$ is the first time value of the pre-determined time interval that causes $t_{0shift}$ to be equal to zero after implementing the time shift using Eq. 2.

The unitless plurality of glucose concentration as a function of time and the shifted times described above can, if desired, be employed in subsequent steps of process 100 in place of the herein described plurality of glucose concentrations as a function of time to avoid complications during mathematical model fitting (for example, during steps 120 and 130 of method 100).

Subsequently, at step 120, a first glucose prediction equation that is a fit to the plurality of glucose concentrations as a function of time is derived, with the fit being based on a first mathematical model. For example, the first glucose prediction equation may be a linear equation fit to the plurality of glucose concentration as a function of time. Such a first glucose prediction equation is illustrated by the following:

$$g1(t) = at + b \qquad \text{Eq. 3}$$

where:

$g1(t)$ is the predicted glucose concentration at time t derived using the first glucose prediction equation;

a is a constant value that represents a slope, and b is a constant value that represents an intercept.

One skilled in the art will recognize that the constants a and b can be derived from the plurality of glucose concentrations as a function of time using any suitable mathematical modeling technique and, if desired, any suitable automated technique such as a combination of software and a computer processor. Nonlimiting examples of suitable mathematical techniques include spline extrapolation, extrapolative smoothing, least squares, higher polynomial extrapolation, and Taylor series expansion.

At step 130, a second glucose prediction equation that is also a fit to the plurality of glucose concentrations as a function of time is derived with the fit being based on a second mathematical model. It should be noted that the second mathematical model is not the same mathematical model as was used in step 120. In other words, the first and second mathematical models are non-identical to one another.

By employing both a first and a second glucose prediction equation, a quantitative merit index (described further herein) is readily calculated. Although a quantitative merit index could theoretically be calculated based on just one glucose prediction equation, the predictive benefit of a merit index is increased when more than one glucose prediction equation is employed (with each of the glucose prediction equations being based on different mathematical models). Moreover, once apprised of the present disclosure, one skilled in the art will recognize that methods according to the present invention can employ more than two glucose prediction equations (for example, a third glucose prediction equation).

For example, the second glucose prediction equation can be derived as a fit to the plurality of glucose concentrations as a function of time based on a quadratic equation. The second glucose prediction equation would then take the following form:

$$g2(t) = ct^2 + dt + e \qquad \text{Eq. 4}$$

where:

$g2(t)$ is the second predicted glucose concentration at time t.

c, d, e are constants, which are derived from the plurality of glucose concentrations as a function of time.

It should be noted that embodiments of the invention are not limited to a linear or a quadratic equation for the derivation of the first and second glucose prediction equations and that other mathematical models may be used to fit the plurality of glucose concentrations as a function of time. For example, the first and second glucose prediction equations equation may be based on mathematical models (and be in the form of) in the form of a cubic equation (Eq. 5 below), one term power function (Eq. 6 below), two term power function (Eq. 7), one term exponential function (Eq. 8), and a two term exponential function (Eq. 9).

$$g(t) = at^3 + bt^2 + ct + d \qquad \text{Eq. 5}$$

$$g(t) = at^b \qquad \text{Eq. 6}$$

$$g(t) = at^b + c \qquad \text{Eq. 7}$$

$$g(t) = ae^{bt} \qquad \text{Eq. 8}$$

$$g(t) = ae^{bt} + ce^{dt} \qquad \text{Eq. 9}$$

where:

t = the variable time;

a, b, c and d represents constants of their respective equations; and e represents an exponential function.

However, for predetermined time intervals of approximately 30 minutes it is expected that glucose concentrations will typically not experience more than one change of direction (i.e., from falling to rising or the reverse). Therefore, the use of cubic polynomial or higher equations/models may introduce complexity and produce poor results when the plurality of glucose concentration is noisy and/or contains unreliable data points. Moreover, linear and quadratic equations/models have the benefit of being robust when applied to noisy data. In addition, the quadratic equation will accommodate a change in direction of glucose concentration while a linear equation is compatible with stagnant glucose concentrations. The use of a linear equation and a quadratic equations/models (as described above), therefore, provides for predictive robustness and accuracy.

A first predicted glucose concentration at a predetermined future time is then calculated using the first glucose prediction equation (see step 140 of FIG. 1). Given that this glucose concentration is associated with a future time (i.e., a time following the end of the measurement duration), its calculation can be considered an extrapolation. The predetermined future time point is referred to as $t_f$ and the first predicted glucose concentration is $g1(t_f)$.

A second predicted glucose concentration at the same predetermined future time is then calculated using the second glucose prediction equation, as set forth in step 150 of FIG. 1. Given that this glucose concentration is associated with a future time (i.e., a time following the end of the measurement duration), its calculation can also be considered an extrapolation. The predetermined future time point is again $t_f$ and the second predicted glucose concentration is $g2(t_f)$.

The predetermined future time point can be any suitable future time point. For example, the predetermined future time point can be in the range of about ten minutes to about thirty minutes following the end of the predetermined time duration during which measurements are made. Factors to consider when predetermining the future time are (i) the percentage of false alarms generated by the method that are considered acceptable for the user since such a may increase with an increase in the future time point value and (ii) the effective response time of a CGM to changing glucose concentrations. A lower limit for the predetermined future time point can, if desired, be greater than the effective response time of the CGM.

An average predicted glucose concentration and a merit index based on the first and second predicted glucose concentrations are calculated in step 160. For example, the first predicted glucose concentration $g1(t_f)$ and the second predicted glucose concentration $g2(t_f)$ may be averaged to form an average predicted glucose concentration.

Moreover, the merit index is calculated based on a degree of correlation between the first predicted glucose concentration and the second predicted glucose concentration. For example, a merit index M may be calculated based on a ratio of the first predicted glucose concentration $g1(t_f)$ and the second predicted glucose concentration $g2(t_f)$. For example, the merit index M may be the absolute difference or percent difference between the first predicted glucose concentration $g1(t_f)$ and the second predicted glucose concentration $g2(t_f)$. Eqs. 10 and 11 define one embodiment of a merit index M.

$$M = g2(t_f) - g1(t_f)/g2(t_f), \text{ if } g2(t_f) \geq g1(t_f) \qquad \text{Eq. 10}$$

$$M = g1(t_f) - g2(t_f)/g1(t_f), \text{ if } g2(t_f) < g1(t_f) \qquad \text{Eq. 11}$$

The merit index essentially serves as a measure of confidence in the first and second predicted glucose concentrations. Therefore, any suitable method known to those of skill in the art for calculating a measure of confidence can be employed to calculate the merit index based on the first and second predicted glucose concentrations.

Figure 2:
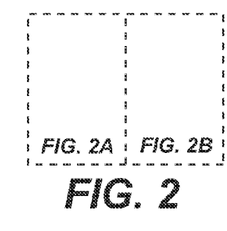
FIG. 2 is a Hidden Markov Model emission matrix table relevant to the process of FIG. 1.
Figure 2A:
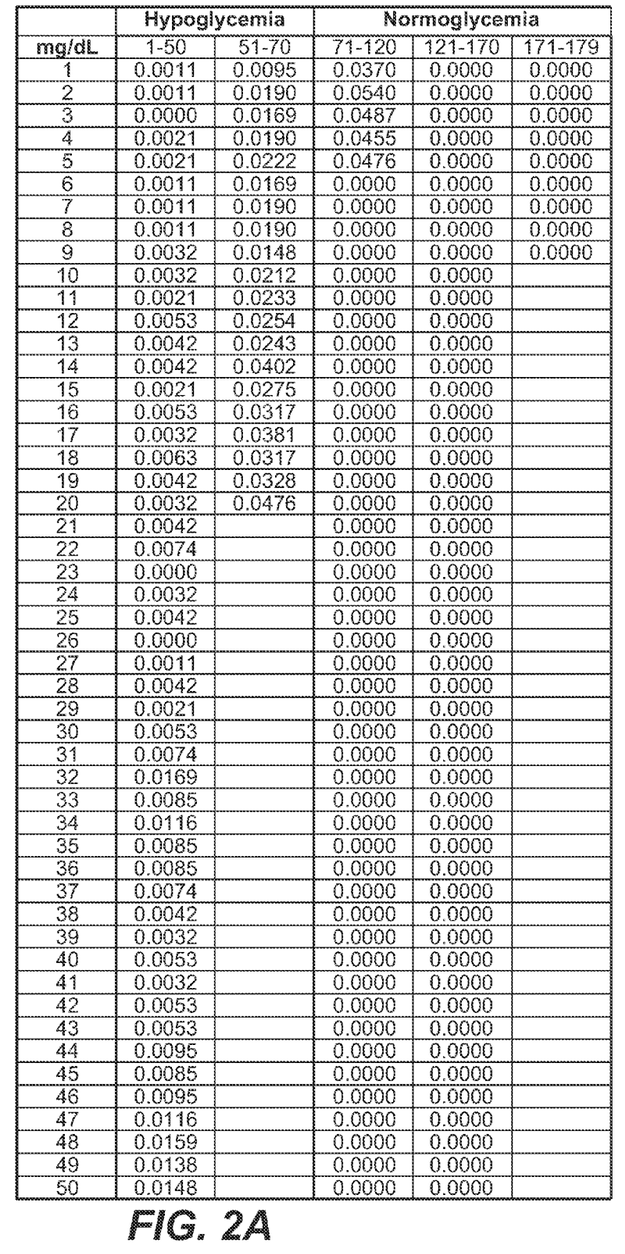

Subsequently, at step 170, the plurality of glucose concentrations as a function of time, the average predicted glucose concentration and the merit index are input into a trained model (such as a Hidden Markov Model HMM, Artificial Neural Network (ANN) model or Bayesian model) that outputs a set of glucose concentration probabilities for the predetermined future time. The set of glucose concentration probabilities can cover, for example, a range of glucose concentrations from about 1 mg/dL to about 620 mg/dL. This set of probabilities is also referred to as an emission matrix. FIG. 2 is an exemplary Hidden Markov Model derived emission matrix table relevant to the process of FIG. 1 that includes the probability of each glucose concentration occurring at the predetermined future time point over a range of glucose concentration in increments of one mg/dL. The table of FIG. 2 is divided into a hypoglycemic range (1 mg/dL-70 mg/dL), an euglycemic range (71 mg/dL-179 mg/dL), and a hyperglycemic range (180 mg/dL-621 mg/dL).

It has been determined that a HMM is especially well suited for glucose concentration (i.e., glycemic state) prediction because an emission sequence that is output from a HMM can be used without knowledge of the state sequence of the user's glycemic process. In other words, the probability of a user achieving a particular glucose concentration (i.e., being in a particular glycemic state at a future time) can be estimated without knowledge of the actual cause of transition to that glucose concentration. An HMM assumes that the plurality of glucose concentrations collected during the predetermined time duration are indicative of an actual cause of a change in glucose concentration at a future time point, although that cause is unknown or "hidden." Thus, the "hidden" actual cause can be modeled indirectly by using the plurality of glucose concentrations collected over the predetermined time period.

One skilled in the art will recognize that a conventional HMM would employ only a time series input (e.g., a plurality of glucose concentrations as a function if time) to output a complete set of probabilities for a future time. However, methods according to embodiments of the present invention also input a merit index and the average predicted glucose concentration into a trained model (such as an HMM model). These two inputs are employed to define the set of glucose concentration probabilities for the predetermined future time such that the set is centered about the average predicted glucose concentration and covers a range that is function of the merit index. For example, the range can be increased when the merit index indicates less confidence in the average predicted glucose concentration and the range can be decreased when the merit index indicates more confidence in the average predicted glucose concentration.

Assuming, for example, that the average predicted glucose concentration is 85 mg/dL, the set of glucose concentration probabilities is limited such that the set is centered on 85 mg/dL and has a range that is a function of the merit index. The range (R) can, for example, be set using the following equation:

$$R = +/-(20\%(M)) \qquad \text{Eq. 12}$$

Assuming for the sake of illustration that M is 1.0, then the range would be +/−20%, i.e., 85 mg/dL+/−17 mg/dL. The trained model would then output a set glucose concentration probabilities for the predetermined future time for glucose concentrations in the range of 85+/−17 mg/dL (i.e., essentially between 67 mg/dL and 103 mg/dL in the table of FIG. 2).

Subsequently, in step 180 of method 100, the user's future glycemic state at the predetermined future time is predicted based on the set of glucose concentration probabilities. For example, a hypoglycemic state can be defined as glucose concentrations in the range of 1 mg/dL to 80 mg/dL. If desirable based on the merit index and the average predicted glucose concentration, the set of probabilities within this range can be summed together to form a summation that represents the probability that a user will be in a hypoglycemic state at the predetermined future time. If the summation is greater than a pre-determined threshold (for example, a predetermined threshold of 50%), then a hypoglycemic alarm could be triggered. Similarly, the hyperglycemic glucose concentration range may be used for predicting hyperglycemia.

Moreover, a prediction for any glucose concentration range (and glycemic state subranges within that range) of interest can be made using the techniques described immediately above. For example, returning to the assumption above that the average predicted glucose concentration is 85 mg/dL, the merit index is 1.0 and Eq. 12 is employed, the following set of glucose concentration probabilities could be used to predict the user's future glycemic state:

Hypoglycemic subrange (>67 to 70 mg/dL)=15.0
Euglycemic subrange (>70 through <103 mg/dL)=23.3
Hyperglycemic subrange (>180 mg/dL and out of range of interest)=0

Normalized to sum to 100%, the probabilities are:
Hypoglycemic subrange (>67 to 70 mg/dL)=39.2%
Euglycemic subrange (>70 through <103 mg/dL)=60.8%
Hyperglycemic subrange (>180 mg/dL and out of range of interest)=0%

Such normalized probabilities can be compared to predetermined thresholds for purposes of alarm triggering.

One skilled in the art will recognize that a Hidden Markov Models is a mathematical model for estimating a probability for a particular state being achieved in a stochastic process. Data (such as a plurality of glucose concentrations as a function of time) are input into a Hidden Markov Model to generate an output consisting of the probability for each state that may be achieved. Hidden Markov Models suitable for use in embodiments of the present invention can be suitably trained (i.e., created) using a plurality of diabetic subjects over a period of time who are subject to everyday conditions. For example, about 7 or more people with diabetes may have their glucose concentration monitored for about 8 days to about 9 days. The people with diabetes may be monitored at a measurement rate of about 0.2 measurements per minute to about 1 measurement per minute using a commercially available Guardian® RT Continuous Monitoring System (Medtronic MiniMed, Northridge, Calif. 91325-1219).

For training the Hidden Markov Model, each person with diabetes may be monitored using three Guardian® Continuous Monitors over the 8 to 9 day period, with each monitor being used for about 72 hours. Although the Guardian® RT Continuous Monitoring System was used to the clinical date used to train the Hidden Markov Model employed to generate FIG. 2 and FIG. 3, other suitable CGMs or methods may be employed to generate HMMs for use in the present invention. The Hidden Markov Model of FIG. 3 was trained using the collected glucose concentrations and employing the "Statistics Toolbox" in MATLAB (R2006b, MathWorks, Natick, Mass. 01760-2098).

Figure 3:
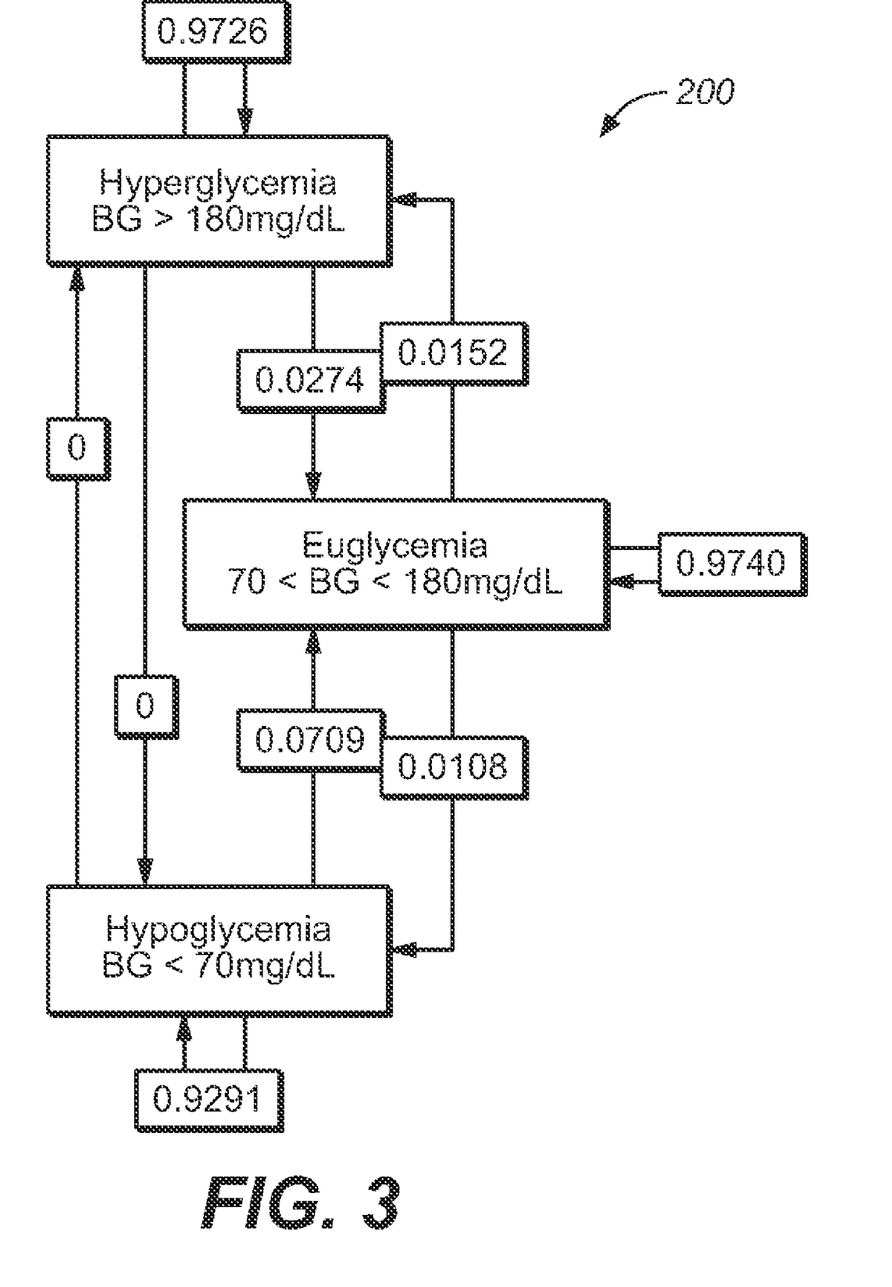
FIG. 3 depicts an exemplary Hidden Markov Model (HMM) that shows a plurality of probabilities for transitioning between glycemic states that is relevant to the process of FIG. 1.

FIG. 3 depicts an exemplary Hidden Markov Model (HMM) that shows a plurality of probabilities for transitioning between three glycemic states that is relevant to the process of FIG. 1. The three glycemic states are hypoglycemic, euglycemic, and hyperglycemic. For each of the three states, a probability is shown that represents the likelihood of a particular state transitioning to another state. For instance, FIG. 3 illustrates that a user in a hyperglycemic state has a 97.26% chance of remaining in the hyperglycemic state, a 2.74% chance of transitioning to the euglycemic state, and a 0% chance of transitioning to the hypoglycemic state. A user in a euglycemic state has a 97.4% chance of remaining in the euglycemic state, a 1.52% chance of transitioning to the hyperglycemic state, and a 1.08% chance of transitioning to the hypoglycemic state. A user in a hypoglycemic state has a 92.91% chance of remaining in the hypoglycemic state, a 7.09% chance of transitioning to the euglycemic state, and a 0% chance of transitioning to the hyperglycemic state. For every predetermined time duration, methods according to embodiments of the present invention can employ an HMM to output an emission matrix that describes the probability of a user transitioning to an array of possible glucose concentration (i.e., possible glycemic states) at a predetermined future time point.

Embodiments of the present invention are beneficial in that a user's future hypoglycemic state (or other glycemic state) can be accurately, quickly and repeatedly predicted based only on prior glucose measurements from the user. Furthermore, embodiments of the present invention are capable of predicting hypoglycemia in a robust manner that is not significantly influenced by noise in the measured glucose concentration measurements due to the employment of a trained model (such as a Hidden Markov Model).

Figure 4:
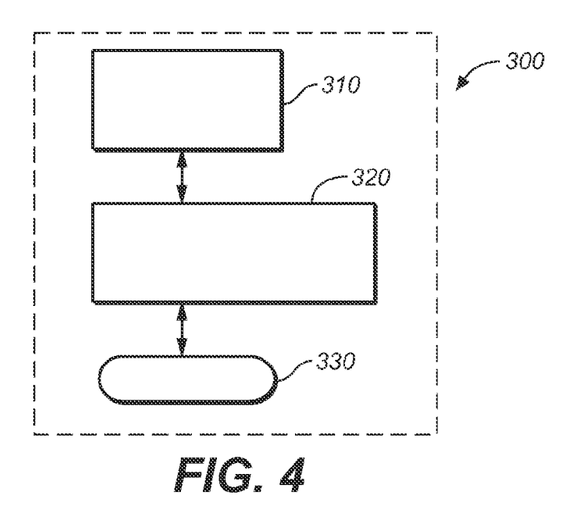
FIG. 4 is a simplified block diagram of a medical device for predicting a user's future glycemic state according to an embodiment of the present invention.

FIG. 4 is a simplified block diagram of a medical device 300 (within the dashed lines) for predicting a user's future glycemic state according to an embodiment of the present invention. Medical device 300 includes a memory module 310, a processor module 320 and a user alert module 330. The double-headed arrows of FIG. 4 indicate that each of the modules is in operative communication with the other modules be it by wired transmission, wireless transmission or other suitable means.

Memory module 310 is configured to receive and store a plurality of glucose concentrations as a function of time that were generated by a continuous glucose monitor. Memory module 310 can be any suitable memory module including memory modules that employ integrated circuits (e.g., DRAM and SRAM based memory modules) and/or optical memory technologies.

Processor module 320 is configured to: (i) derive a first glucose prediction equation that is a fit to the plurality of glucose concentrations as a function of time stored in the memory module, the fit being based on a first mathematical model; (ii) derive a second glucose prediction equation that is a fit to the plurality of glucose concentrations as a function of time, the fit being based on a second mathematical model; (iii) calculate a first predicted glucose concentration at a predetermined future time using the first glucose prediction equation; (iv) calculate a second predicted glucose concentration at the predetermined future time using the second glucose prediction equation; (v) calculate an average predicted glucose concentration and a merit index based on the first and second predicted glucose calculations; (vi) input the plurality of glucose concentrations as a function of time, the average predicted glucose concentration and the merit index into a trained model that outputs a set of glucose concentration probabilities for the predetermined future time; and (vii) predict user's future glycemic state based on the set of glucose concentration probabilities.

User alert module 330 is configured to alert the user in a manner dependent on the glucose probabilities for the predetermined future time. User alert module 330 can be, for example, a visual display, an audible alarm generation device, a tactile sensation generation device or any combination thereof.

Figure 5:
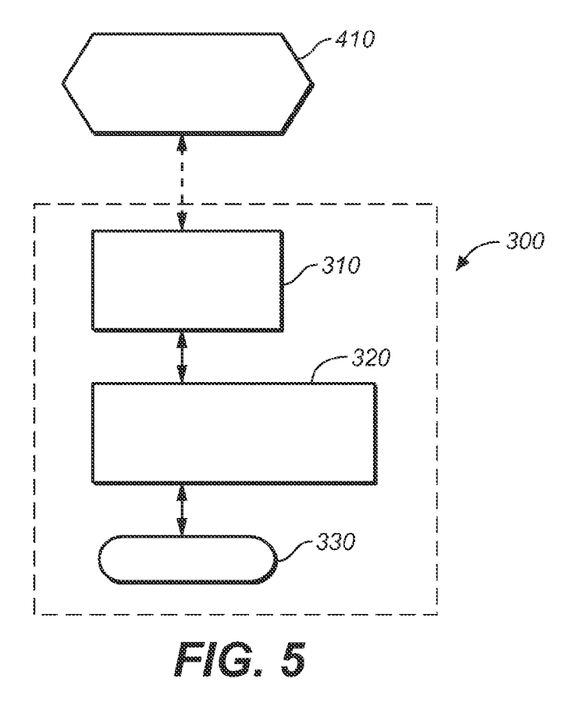
FIG. 5 is a simplified block diagram of a kit for predicting a user's future glycemic state according to an embodiment of the present invention.

Medical device 300 (and kit 400 described further below) implement methods according to the present invention including, for example method 100 described above. Therefore, characteristics, benefits, and aspects of described with respect to methods according to the present invention can be incorporated into medical devices and kits of the present invention.

FIG. 5 is a simplified block diagram of a kit 400 for predicting a user's future glycemic state according to an exemplary embodiment of the present invention. Kit 400 includes a continuous glucose monitor 410 and a medical device 300. Medical device 300 was described above. The dashed double-headed arrow of FIG. 5 indicates that the continuous glucose monitor is in operative communication with medical device 300 by, for example, a suitable wired or wireless communication technique.

Continuous glucose monitor 410 is configured to measure a user's glucose concentration at intervals over a predetermined time duration, thereby generating a plurality of glucose concentrations as a function of time. Continuous glucose monitoring 410 can be any suitable CGM known to one skilled in the art.

A kit for predicting a user's future glycemic state includes a continuous glucose monitor and a medical device. The continuous glucose monitor is configured to measure a user's glucose concentration at intervals over a time duration, thereby generating a plurality of glucose concentrations as a function of time. The medical device includes a memory, processor and user alert modules. The memory module is configured to receive and store the plurality of glucose concentrations generated the continuous glucose monitor. The processor module is configured to derive first and second glucose prediction equations that are fits to the plurality of glucose concentrations stored in the memory module with the fits being based on first and second mathematical models, respectively. The processor module is also configured to calculate first and second predicted glucose concentrations at a future time using the first and second glucose prediction equations, respectively, and to also calculate an average predicted glucose concentration and a merit index based on the first and second predicted glucose calculations. The processor module is further configured to input the plurality of glucose concentrations as a function of time, the average predicted glucose concentration and the merit index into a trained model (e.g., a Hidden Markov Model) that outputs a set of glucose concentration probabilities for the future time and to then predict the user's future glycemic state based on the set of glucose concentration probabilities. The user alert module is configured to alert the user in a manner dependent on the predicted user's future glycemic state.

A kit for predicting a user's future glycemic state comprises a continuous glucose monitor configured to measure a user's glucose concentration at intervals over a predetermined time duration, thereby generating a plurality of glucose concentrations as a function of time; and a medical device for predicting a user's future glycemic state that includes: a memory module; a processor module; and a user alert module, wherein the memory module is configured to receive and store a plurality of glucose concentrations as a function of time that were generated by a user's use of the continuous glucose monitor, and wherein the processor module is configured to: derive a first glucose prediction equation that is a fit to the plurality of glucose concentrations as a function of time stored in the memory module, the fit being based on a first mathematical model; derive a second glucose prediction equation that is a fit to the plurality of glucose concentrations as a function of time, the fit being based on a second mathematical model; calculate a first predicted glucose concentration $g1(t_f)$ at a predetermined future time using the first glucose prediction equation; calculate a second predicted glucose concentration $g2(t_f)$ at the predetermined future time using the second glucose prediction equation; calculate an average predicted glucose concentration and a merit index M based on the first and second predicted glucose calculations; input the plurality of glucose concentrations as a function of time, the average predicted glucose concentration and the merit index into a trained model that outputs a set of glucose concentration probabilities for the predetermined future time, predict the user's future glycemic state based on the set of glucose concentration probabilities; wherein the user alert module is configured to alert the user in a manner dependent on the predicted user's future glycemic state.

In the kit, the processor calculates a merit index that is dependent on correlation between the first predicted glucose concentration and the second predicted glucose concentration. The first mathematical model and the second mathematical model employed by the processor are one of a linear model, a quadratic model, a one term power function model, a two term power function model, a one term exponential function model and a two term exponential function model. An example for the trained model employed by the processor includes a Hidden Markov Model (HMM). The processor predicts the probability that the user will be in a hypoglycemic state at the predetermined future time based on the set of glucose concentration probabilities. The user alert module alerts the user when the probability of the user being in a hypoglycemic state is greater than a predetermined threshold probability.

In the kit, the memory module stores a plurality of glucose concentrations as a function of time is in the range of seven to thirst glucose concentrations as a function of time. The processor employs the predetermined future time point is a time in the range of about 10 minutes to about 30 minutes after the predetermined time duration. The interval is in the range of about 0.2 minutes to about 1 minute. The processor module calculates the merit index using the following algorithms:

$$M = g2(t_f) - g1(t_f)/g2(t_f), \text{ if } g2(t_f) \geq g1(t_f)$$

$$M = g1(t_f) - g2(t_f)/g1(t_f), \text{ if } g2(t_f) < g1(t_f)$$

The first mathematical model is a linear model and the second mathematical model is a quadratic model. The set of glucose concentration probabilities is centered on the average predicted glucose concentration and has a range that is dependent on the merit index.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. A medical device for predicting a user's future glycemic state comprising:

a memory module;

a processor module; and a user alert module, wherein the memory module is configured to receive and store a plurality of glucose concentrations as a function of time that were generated by a user's use of a continuous glucose monitor, and wherein the processor module is configured to:

derive a first glucose prediction equation that is a fit to the plurality of glucose concentrations as a function of time stored in the memory module, the fit being based on a first mathematical model;

derive a second glucose prediction equation that is a fit to the plurality of glucose concentrations as a function of time, the fit being based on a second mathematical model;

calculate a first predicted glucose concentration $g1(t_f)$ at a predetermined future time using the first glucose prediction equation;

calculate a second predicted glucose concentration $g2(t_f)$ at the predetermined future time using the second glucose prediction equation;

calculate an average predicted glucose concentration and a merit index M based on the first and second predicted glucose calculations;

input the plurality of glucose concentrations as a function of time, the average predicted glucose concentration and the merit index into a trained model that outputs a set of glucose concentration probabilities for the predetermined future time, predict the user's future glycemic state based on the set of glucose concentration probabilities;

wherein the user alert module is configured to alert the user in a manner dependent on the predicted user's future glycemic state; and wherein the processor module calculates the merit index using the following algorithms:

$$M = g2(t_f) - g1(t_f)/g2(t_f), \text{ if } g2(t_f) \geq g1(t_f)$$

$$M = g1(t_f) - g2(t_f)/g1(t_f), \text{ if } g2(t_f) < g1(t_f).$$

2. The medical device of claim 1 wherein the set of glucose concentration probabilities is centered on the average predicted glucose concentration and has a range that is dependent on the merit index.

3. The medical device of 1 wherein the processor predicts the probability that the user will be in a hypoglycemic state at the predetermined future time based on the set of glucose concentration probabilities.

4. The medical device of claim 3, in which the user alert module alerts the user when the probability of the user being in a hypoglycemic state is greater than a predetermined threshold probability.

5. The medical device of claim 1 wherein the memory module stores a plurality of glucose concentrations as a function of time is in the range of seven to thirty glucose concentrations as a function of time.

6. The medical device of claim 1, in which the processor employs the predetermined future time point is a time in the range of about 10 minutes to about 30 minutes after the predetermined time duration.

7. The medical device of claim 1, in which the interval is in the range from about 0.2 minutes to about 1 minute.

* * * * *